(12) United States Patent
Binmoeller

(10) Patent No.: US 6,228,039 B1
(45) Date of Patent: May 8, 2001

(54) BIOPSY DEVICE

(76) Inventor: Kenneth F. Binmoeller, 12804 Baywind Point, San Diego, CA (US) 92130

( * ) Notice: Subject to any disclaimer, the term of this patent is extended or adjusted under 35 U.S.C. 154(b) by 0 days.

(21) Appl. No.: 09/433,092

(22) Filed: Nov. 3, 1999

Related U.S. Application Data

(63) Continuation of application No. PCT/IB98/00942, filed on May 7, 1998.

(30) Foreign Application Priority Data

May 7, 1997 (DE) .......................................... 297 08 149 U

(51) Int. Cl.[7] .................................................. A61B 10/00
(52) U.S. Cl. ......................... 600/566; 600/564; 600/104; 606/170
(58) Field of Search ................................. 600/104, 106, 600/153, 562, 564, 566, 567; 606/46, 167, 169, 170, 181, 182; 604/22, 19

(56) References Cited

U.S. PATENT DOCUMENTS

| 2,725,878 | 12/1955 | Reiter .................................. 128/305 |
| 4,572,201 | * 2/1986 | Kondo et al. ...................... 128/660 |
| 4,578,061 | 3/1986 | Lemelson .............................. 604/164 |
| 4,700,694 | * 10/1987 | Shishido ............................... 600/106 |
| 4,763,667 | 8/1988 | Manzo ................................... 128/750 |
| 4,982,724 | 1/1991 | Saito et al. ............................ 600/104 |
| 5,060,658 | * 10/1991 | Dejter, Jr. et al. .................... 600/566 |
| 5,234,426 | 8/1993 | Rank et al. .............................. 606/1 |
| 5,342,296 | 8/1994 | Persson et al. ......................... 604/49 |
| 5,342,394 | 8/1994 | Matsuno et al. ..................... 606/213 |
| 5,470,308 | * 11/1995 | Edwards et al. ........................ 604/22 |
| 5,514,111 | * 5/1996 | Phelps ................................... 604/248 |
| 5,601,533 | * 2/1997 | Hancke et al. .................. 604/164.01 |
| 5,601,588 | * 2/1997 | Tonomura et al. ................... 606/185 |
| 5,820,554 | * 10/1998 | Davis et al. .......................... 600/431 |
| 5,830,152 | * 11/1998 | Tao ....................................... 600/562 |
| 5,910,105 | * 6/1999 | Swain et al. ......................... 600/131 |

FOREIGN PATENT DOCUMENTS

| 17 91 178 | 11/1971 | (DE) . |
| 38 44 131 | 7/1989 | (DE) . |
| 44 19 894 | 12/1995 | (DE) . |

* cited by examiner

Primary Examiner—Eric F. Winakur
Assistant Examiner—Charles Marmor, II
(74) Attorney, Agent, or Firm—Frishauf, Holtz, Goodman, Langer & Chick, P.C.

(57) ABSTRACT

The invention relates to a device for performing endoscopic guided fine needle biopsy, in which the needle is automatically controlled by using a pre-biased needle. Upon release of a spring, the needle projects toward tissue, overcoming frictional forces, thanks to high acceleration. This reduces the danger of breaking the needle.

10 Claims, 3 Drawing Sheets

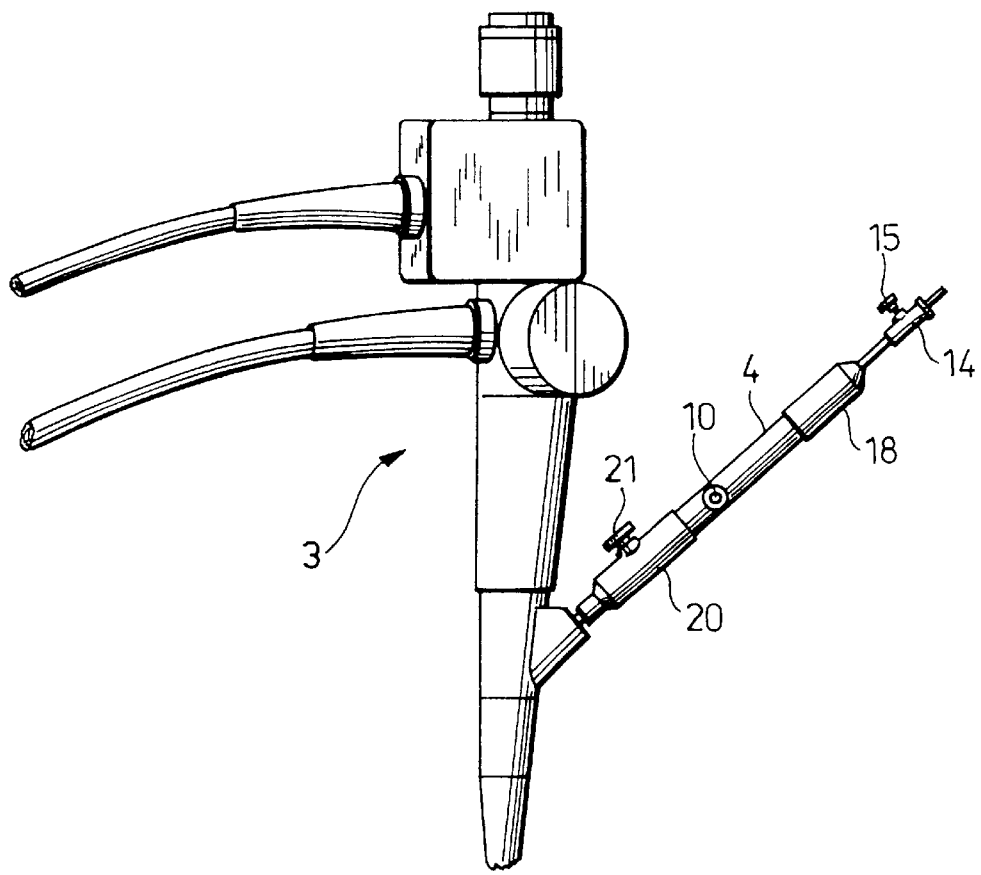

BIOPSY DEVICE

CROSS-REFERENCE TO RELATED APPLICATIONS

This is a continuation application of International Application No. PCT/IB98/00942, filed May 7, 1998, the entire contents of which are incorporated herein by reference.

BACKGROUND OF THE INVENTION

The present invention relates to a device for performing endoscopic guided fine-needle biopsy.

In the medicine it is known that, to collect a tissue sample, a hollow needle is used to puncture tissue and to gain biological material for histological, cytological or genetechnological examinations.

As to the cytological examination, in particular, fine-needle biopsy is known. In this biopsy, cell material is collected by a thin hollow needle by means of suction. Usually the collection of the tissues and the positioning of the hollow needle are monitored with ultrasonic waves. The monitoring by the use of ultrasonic waves is necessary, particularly when it is necessary to collect the tissue from a small region which has been specified.

In case of percutaneous hollow-needle biopsy, the needle is pushed forward through the skin of the patient until it reaches the tissue from which a sample shall be collected. The percutaneous hollow-needle biopsy is suitable for collecting tissue which can be easily accessed, directly through the skin. Ordinary needles have a length of 6 to 10 cm and are monitored by means of an imaging method, such as ultrasonic or computer tomography. The efficiency of the tissue sampling and the efficiency of penetrating hardened tissue can be improved by abruptly pushing the needle if the needle is relatively short. The pushing of the needle can be assisted by a spring force.

Certain tissues are not suitable for being punctured with a percutaneous biopsy needle. This is because the needle cannot reach the tissue. For example, another tissue can block the insertion of the biopsy needle.

Hereto it has been known that a biopsy needle can also be guided through an echo-endoscope, to thereby collect tissues through a hollow organ (Hahlorgan). In this technique, the echo-endoscope possess not only functions as an optical monitor for the puncture, but also is a protecting sleeve and a means for guiding the needle over a long distance and positioning the needle at the sampling position.

The technique of echo-endoscopic fine-needle biopsy is employed to, for example, collect pancreasor lymphatic node tissue. The echo-endoscope which is appropriate for use in this technique has a passage for guiding the biopsy needle. The needle is inserted into the hollow organ, while being guided through the echo-endoscope, until it reaches the sampling position. At the sampling position, the needle is inserted into the tissue and moved back and forth, whereby a sample is separated from the tissue by virtue of a negative pressure. In order to obtain material in a sufficient amount for cytological or histological examination, the needle must be moved back and forth many times.

In this technique, the needle needs to be long enough to have access to the tissue to be sampled, through a hollow organ. This results in some drawbacks. The length of the needle must be greater than the length of the endoscope. For example, tissues must be sampled with needles about 160 cm long, or ten times or more as long as needles for use in percutaneous biopsy.

Some skill is required to operate endoscopes. For example, it is difficult to control the needle in the grip region of an endoscope, in the process of positioning an endoscope. This is true, especially when the needle must be guided along several curves, through a passage formed in the endoscope. The force which is necessary for moving the needle increases as the needle is guided along each curve, due to the frictional forces at the curves. The sum of the frictional forces may become considerable. The user must manually overcome the sum of frictional forces. This makes it difficult to perform a precise operation, causes the danger of breaking the needle, and may result in damage to the echo-endoscope which is a sensitive component.

In addition, the fine needle biopsy relating to echo-endosonography cannot be achieved at all when the tissue to be sampled has a certain hardness, as do pathologically hardened tissues. In this case, the needle is not inserted into the tissue. If the needle is inserted, the pressure applied to it will increase very much. Even in the best case, the needle or the endoscope connected to the needle may avoid contacting the tissue, but the endoscope may nevertheless be damaged.

Even if the tissue is easy to penetrate, the tissue sampled is often not satisfactory. This is especially disadvantageous, when the punctured tissue is intended for a cytlogical or histological examination. Thus, the biopsy needle must be moved back and forth several times to increase the amount of tissue sampled. Even if this technique is applied, it may not possible to sample tissue in a useful amount.

BRIEF SUMMARY OF THE INVENTION

The object of the present invention is to solve the above described problems and to provide an improved endoscopic biopsy device that can be used to sample even hardened or hard tissue.

The solution is achieved by automatically operating the needle and pre-biasing the needle by means of, for example, a spring. As soon as the spring is loosened, the needle thrusts forward into the tissue. By virtue of the inertia of the mass of the echo-endoscope, the needle passes through even hardened tissue. The high acceleration of the needle lessens the bending of the needle and overcomes the frictional forces.

More specifically, according to the device of the present invention, the needle pre-biased rushes forward after a release device provided on the pre-biasing device is operated.

The biopsy needle automated according to the invention can acquire high quality samples, and can penetrate even hardened tissue which cannot be sampled through an endoscope by the use of the conventional manual biopsy needle. As described above, if a manual biopsy needle is used to sample hardened tissue, there is a risk that either the needle or the endoscope will be damaged.

Further, the use of the biopsy needle of the invention results in a considerable increase in the amount of tissues sampled and avoids the undesirable, repeated reciprocating motion required with conventional techniques.

In this case, the needle in the passage formed in the echo-endoscope can be surrounded by a protecting sleeve. Preferably, the sleeve is made of a spiral-type sheath that can be moved independently of the needle. The movable sleeve protects and reinforces the needle and can position the needle appropriately, even after the needle has moved out of the passage provided in the echo-endoscope.

In order to reliably move the biopsy needle forwards and to prevent the pre-biasing device from projecting, the housing of the pre-biasing device can be set into screw engagement with the opening of the passage provided in the echo-endoscope. Adjusting means may precisely adjust the position of the needle and the forward movement of the pre-biasing device.

The device according to a specific embodiment of the invention can also be used for conventional manual sampling of tissue, achieved by reciprocating a biopsy needle, in addition to the function of automatically sampling tissues. Thus, it is possible to sample tissues by (manually) moving the needle back and forth or by (automatically) thrusting the needle forward, before or during the sampling of tissues.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 shows the pre-biasing device located at the operating end of the echo-endoscope.

DETAILED DESCRIPTION OF THE INVENTION

Figure 1:
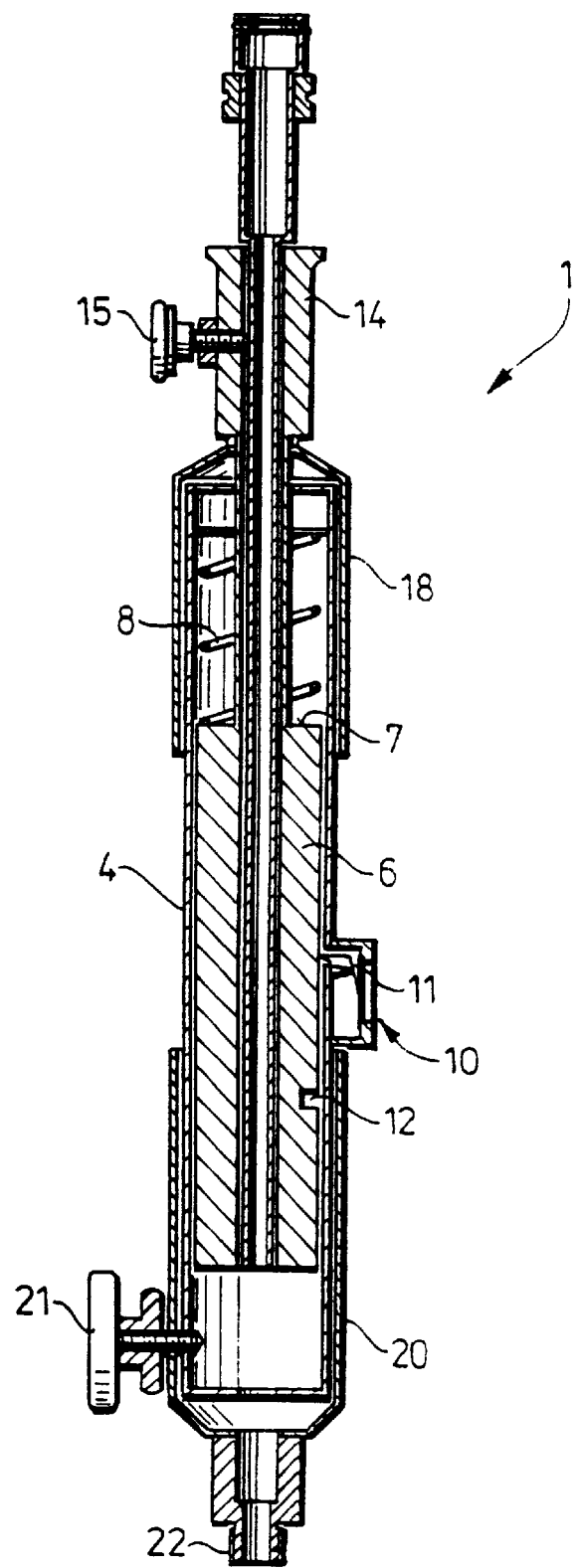
FIG. 1 is a schematic view of the pre-biasing device of the biopsy device according to the invention.
Figure 2:
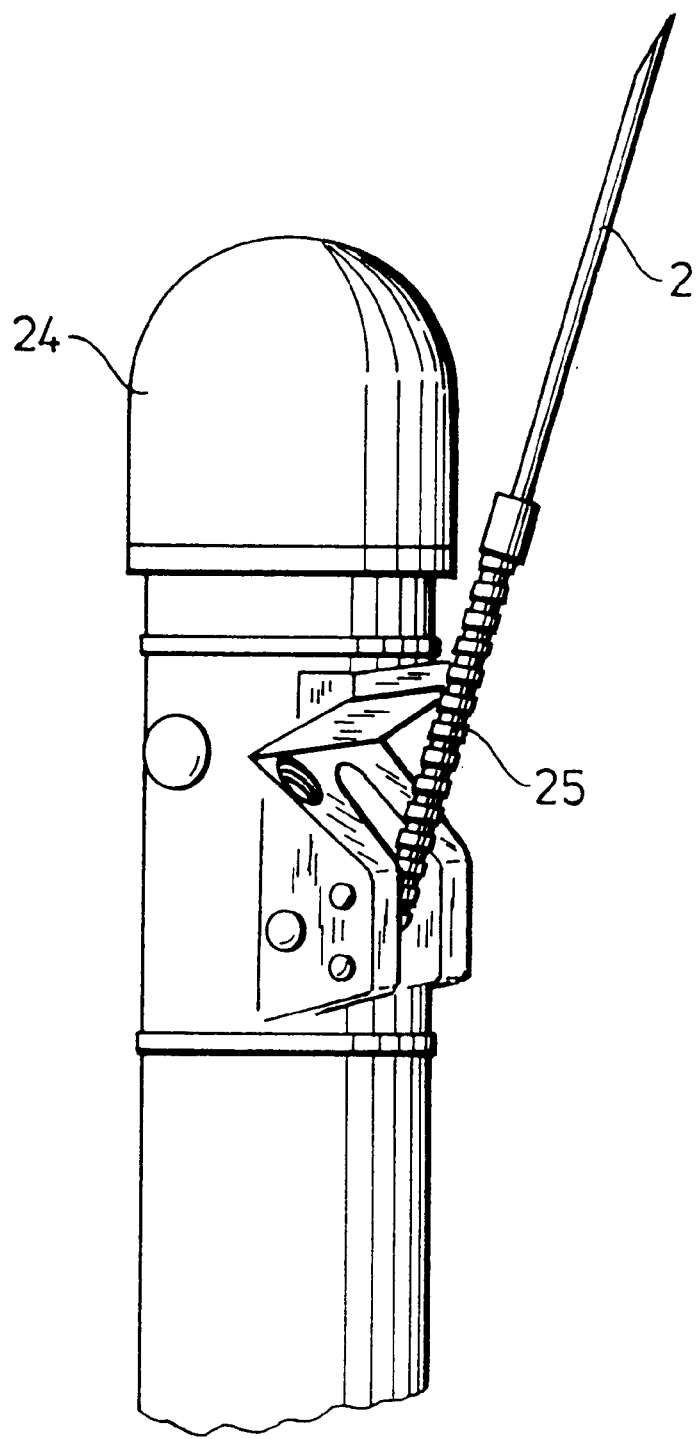
FIG. 2 shows the biopsy needle projecting from the examination end of the echo-endoscope.

The biopsy needle comprises an operating- and pre-biasing device 1. The device 1 has a main cylinder 4, in which a sliding piston 6 is provided. The sliding piston 6 has a projection 7 on its top end. To the projection 7 there is attached a spring 8 for pre-biasing the needle 2. A release device 10 having a spring 11 is provided on the main cylinder. The spring 11 is set into a groove 12 made in the slide piston 6, when the biopsy needle 2 or the slide piston 6 is biased. At the end of the slide piston 6, which is distant from the needle, a grip 14 is provided to move the piston 6, thereby to perform automatic biopsy. On the grip a stop pin 15 is provided, by which the biopsy needle 2 is secured. As long as the spring 8 is released, the grip 14 remains in contact with a calibration cap 18. The position of the calibration cap 18 is changed to adjust the end position of the piston 6 and, hence, the penetration depth of the biopsy needle 2.

An outer sleeve 20 is provided on the end of the main cylinder 4, which is near the needle. This end of the cylinder 4 holds the pre-biasing and control device in the needle passage provided in the endoscope. The main cylinder 4 is fastened to the outer sleeve 20 by means of a stop pin or screw 21. The outer sleeve 20 is fixed in the open end (inlet port) of the needle passage of the echo-endoscope 3 by means of a screw attachment 22.

As the echo-endoscope, Olympus GF-VU30PTM, manufactured by Olympus Optical Company in Tokyo, Japan, can be used. This echo-endoscope comprises a needle passage having a diameter of 2.8 mm and an outlet port immediately adjacent to the fiberglass optic. The angle of departure of the needle is adjusted at the echo-endoscope. A detection probe 24 is provided at the end of the echo-endoscope and is surrounded by a latex-balloon. The latex-balloon can be filled with water during the use of the echo-endoscope. The water can serve as medium between the detection probe 24 and, for example, the intestinal wall.

The biopsy needle 2 extends through a spiral-type outer sheath 25. The needle 2 is inserted into the echo-endoscope by the operating- and pre-biasing device 1 until it projects, along with the sleeve, from the lower end of the echo-endoscope. In this case, it would be desired that the needle tip be beveled and that the distal end of the needle 2 be sand-blasted to improve the resolution of ultrasonic imaging.

A dull stylette is located in the hollow needle and projects by 2 mm from the open end of the needle.

The near end of the biopsy needle 2, which is to be inserted into the operating- and pre-biasing device 1 is set in screw engagement with the near end part of the operating- and pre-biasing device 1.

In the device according to the invention, the biopsy needle 2 can be manually moved back and forth by loosening the stop pin 15 provided on the grip 14. The position of the needle can therefore be manually adjusted, too, as is the conventional device.

The slide piston 6 may be drawn back greatly. If so, the groove 12 moves toward the spring 11, compressing the coil spring 8. When the spring 11 comes into engagement with the groove 12, the biopsy needle 2 is pre-biased and can be fast moved forward by the release device 10. The calibrating sleeve 18 adjusts the depth of penetration of the biopsy needle 2. A coarse adjustment is possible in accordance of the depth of insertion of the main cylinder 4. At this time, the main cylinder 4 is fixed in place by stop pin or screw 21.

A quick and accurate adjustment of the biopsy needle is performed by the outer sleeve 20 provided at the end of the main cylinder 4. Once the stop pin or screw 21 is loosened, while the stop pin 15 remains tightened, the spiral-type sheath 25 attached to the main cylinder 4 and the biopsy needle 2 secured to the slide piston 6 are inserted together into the outer sleeve 20 until they become visible in the echo-endoscope. Thereafter, the stop pin or screw 21 is tightened, whereby the calibrating sleeve 18 adjusts the depth of penetration with precision. The stylette is drawn a little from the hollow needle, releasing the sharp end of the hollow needle. The sharp end of the needle first penetrates tissue, such as the intestinal wall, and then comes close to the tissue which is to be punctured.

As soon as the needle reaches the tissue to be punctured, the stylette is removed and an injector for generating a low pressure, for example, is set into contact with the other end of the hollow needle 2.

The stop pin 15 provided on the grip 14 may be loosened to insert the needle into the tissue to be punctured. To accomplish manual puncture, the stop pin 15 may be loosened and the biopsy needle 2 may be moved back and forth with respect to the main cylinder 4. When the manual puncture is difficult to achieve or when the tissue is hard to penetrate, the release device 10 releases the elastic spring, with the needle projecting forward into the hardened tissue.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A tissue sampling device adapted for use in an endoscope, said device comprising:

a hollow needle surrounded by an outer sheath;

pre-biasing means for pre-biasing the hollow needle forward in an axial direction of the tissue-sampling device;

release means for causing the pre-biased hollow needle to be released so that the hollow needle is projected forward in the axial direction of the tissue-sampling device at a high velocity; and an attachment arranged to fix the tissue-sampling device at an inlet port of a needle passage of the endoscope.

2. A device according to claim 1, wherein the pre-biasing means comprises an outer sleeve adapted to enable adjustment of an exposed portion of the outer sheath.

3. A device according to claim 1, wherein the pre-biasing means comprises a calibrating sleeve adapted to enable precise adjustment of a depth of insertion of the hollow needle into a tissue sample.

4. A device according to claim 1, wherein the pre-biasing means comprises a spring that is connectable to and disconnectable from the hollow needle, and wherein when the spring is disconnected from the hollow needle, the hollow needle is adapted to be manually controlled.

5. A device according to claim 4, wherein the spring is a coil spring.

6. A device according to claim 1, wherein the hollow needle comprises a distal end portion that is treated by sand-blasting.

7. A device according to claim 1, wherein the hollow needle comprises a distal end portion that protrudes past a distal end portion of the outer sheath surrounding the hollow needle when the hollow needle is projected forward in the axial direction of the tissue-sampling device.

8. A device according to claim 7, wherein the outer sheath is movable in a needle passage of the endoscope independently of the hollow needle.

9. A device according to claim 1, wherein the device is adapted for used in an echo-endoscope.

10. A device according to claim 1, wherein said attachment comprises a screw attachment.

* * * * *